(12) United States Patent
Lindeman (10) Patent No.: US 7,363,822 B2
(45) Date of Patent: Apr. 29, 2008

(54) TECHNIQUE FOR APPLYING DIRECT RESISTANCE HEATING CURRENT TO A SPECIFIC LOCATION IN A SPECIMEN UNDER TEST WHILE SUBSTANTIALLY REDUCING THERMAL GRADIENTS IN THE SPECIMEN GAUGE LENGTH

(75) Inventor: Norman A. Lindeman, Sand Lake, NY (US)

(73) Assignee: Dynamic Systems Inc., Poestenkill, NY (US)

( * ) Notice: Subject to any disclaimer, the term of this patent is extended or adjusted under 35 U.S.C. 154(b) by 58 days.

(21) Appl. No.: 11/351,524

(22) Filed: Feb. 10, 2006

(65) Prior Publication Data
US 2006/0180577 A1    Aug. 17, 2006

Related U.S. Application Data

(60) Provisional application No. 60/652,491, filed on Feb. 11, 2005.

(51) Int. Cl.
*G01N 3/08* (2006.01)
(52) U.S. Cl. ...................................................... 73/818
(58) Field of Classification Search .................. 73/774, 73/818–825
See application file for complete search history.

(56) References Cited

U.S. PATENT DOCUMENTS

| | | | |
|---|---|---|---|
| 3,611,787 A | | 10/1971 | D'Annessa et al. |
| 4,618,267 A | * | 10/1986 | Burke et al. .................. 374/50 |
| 5,055,648 A | * | 10/1991 | Iceland et al. ............... 219/601 |
| 5,202,542 A | * | 4/1993 | Ferguson ..................... 219/50 |
| 5,315,085 A | * | 5/1994 | Ferguson ..................... 219/50 |
| 5,481,086 A | * | 1/1996 | Ferguson ..................... 219/385 |
| 5,959,215 A | * | 9/1999 | Ono et al. ..................... 73/798 |
| 6,166,360 A | * | 12/2000 | Ruffini et al. ............... 219/639 |
| 6,422,090 B1 | * | 7/2002 | Ferguson ..................... 73/795 |
| 7,107,857 B2 | * | 9/2006 | Ferguson et al. ............. 73/818 |
| 7,137,306 B2 | * | 11/2006 | Ferguson et al. ............. 73/818 |
| 2005/0011274 A1 | * | 1/2005 | Ferguson et al. ............. 73/818 |
| 2005/0011275 A1 | * | 1/2005 | Ferguson et al. ............. 73/818 |

FOREIGN PATENT DOCUMENTS

| | | |
|---|---|---|
| WO | WO 94/14046 | 6/1994 |
| WO | WO 2005/010500 | 2/2005 |

* cited by examiner

*Primary Examiner*—Edward Lefkowitz
*Assistant Examiner*—Freddie Kirkland, III
(74) *Attorney, Agent, or Firm*—Michaelson & Associates; Peter L. Michaelson (57) ABSTRACT

A technique for imparting direct resistance heating to a gauge length of a conductive metallic specimen under test and which can be used to add an independent dynamic thermal capability to a mechanical material test system. Specifically, a pair of, e.g., conductive collars, each of which encircles and abuts against a corresponding portion of the external surface of the specimen near an opposing end of its gauge length and inward of a corresponding grip. Each collar imparts additional self-resistive heat to the specimen along a circumferential collar/specimen interface. This additional heat appreciably reduces or cancels thermal gradients otherwise arising from self-resistive heating across the gauge length as well as compensates for thermal losses in each specimen end section. Through this arrangement, each specimen end section and the grips are not appreciably heated as the gauge length heats. The amount of additional heat is set by selecting a collar material to have a desired resistivity and also by appropriately dimensioning each collar.

23 Claims, 3 Drawing Sheets

TECHNIQUE FOR APPLYING DIRECT RESISTANCE HEATING CURRENT TO A SPECIFIC LOCATION IN A SPECIMEN UNDER TEST WHILE SUBSTANTIALLY REDUCING THERMAL GRADIENTS IN THE SPECIMEN GAUGE LENGTH

CLAIM TO PRIORITY

This application claims priority of a now abandoned United States provisional patent application entitled "DIRECT RESISTANCE HEATING METHOD FOR APPLYING CURRENT TO A SPECIFIC LOCATION IN A MATERIAL", assigned Ser. No. 60/652,491 and filed Feb. 11, 2005; and which is incorporated by reference herein.

BACKGROUND OF THE INVENTION

1. Field of the Invention

The present invention relates to a technique, specifically apparatus and an accompanying method, for imparting direct resistance heating to a specific location in, for example, a conductive metallic specimen under test and which is particularly, though not exclusively, suited for use in adding an independent dynamic thermal capability to a mechanical test system. Advantageously, through use of the invention, axial thermal gradients that would otherwise appear along a gauge length of the specimen while it self-resistively heats can be set to a desired level or even substantially eliminated altogether, while specimen end sections, outside the gauge length, and grips, that hold opposing ends of the specimen, are not appreciably heated.

2. Description of the Prior Art

Metallic materials play an indispensable role as an essential component of an enormous number of different products and thus clearly occupy an important role in the world economy. As such, their properties and costs both to manufacture and utilize must be carefully controlled to maximize their utility and value. Doing so is commonly accomplished through tests and physical simulation of both metal manufacturing and fabrication processes and applications. More recently, computer simulation, relying on data gained through physical simulation, has been used in defining and selecting an appropriate metallic material for a given application in view of its requirements and the expected behavior, as reflected by that data, of various materials then under consideration.

Thermo-mechanical test systems currently exist which, under computer control, simultaneously treat metallic specimens to both thermal and mechanical pre-defined test procedures (commonly called "programs") in order to accurately simulate various manufacturing and processing steps.

Within a physical simulation system, a mechanical system is used to controllably deform metallic test specimens. The deformation is often provided by servo-controlled hydraulic units or electric motor driven systems which can impart tensile, compressive or torsion forces on a specimen to controllably strain and/or deform it. Further, through the mechanical system, a tension, compression or torsion deformation program may be repeated several times on the same specimen and at different amounts and rates. Test specimens, used in deformation studies, typically fall within a variety of sizes and shapes depending on the type of mechanical test to which the specimen is to be subjected.

The specimen is held, near its ends, between two grips which together mechanically restrain the specimen and provide electrical and thermal contact with opposing ends of the specimen. Thermal heating current is routed through the grips. Depending on a test to be done, a resulting thermal gradient, occurring lengthwise through the specimen may be adjusted by changing grip materials and/or shape of the specimen, to create, on the one hand, a very steep gradient or, on the other hand, a very shallow gradient, or any desired value there between, or even no appreciable gradient at all.

In many types of tests that require specimen heating, it is desirable to have as uniform a temperature as possible across a region of the specimen which is of interest in the test methodology (this region being commonly referred to as a "gauge length"). However, owing to the elevated temperatures involved, the grips which are employed to hold the specimen at its ends typically need to be water cooled so that mechanical properties of the grips are not compromised at those temperatures. In addition, the end section of the specimen situated between the gauge length and each grip should be mechanically strong to prevent that section from deforming which, should that occur, will adversely affect the test results. Consequently, specimens are typically designed with a reduced diameter gauge length, as compared to the diameter of each end section, such that the gauge length will deform first when mechanical work is applied to the specimen.

One of three types of thermal systems is generally used in a physical simulation system: a furnace, an induction heater or self-resistive heating.

Furnaces, which rely on establishing convective heat currents from a heat source, often radiant, to a specimen surface and from there inward into the specimen, provide relatively slow heating rates. Two generally used methods exist for heating the specimen with a furnace. In one method, an entire specimen and its grips, with the specimen then being held by the grips, are fully inserted in the furnace. The furnace then heats both the specimen and the grips. Hence, the entire portion of the specimen lying between the grips is considered the gauge length. Through another method, a furnace is sized so that only a reduced diameter gauge length of the specimen is enclosed in the furnace but not the grips. The furnace is typically built with three internal heating zones traversed by the entire gauge length. Both end zones of the furnace are typically hotter than a center zone. This additional heating capability provided to ends of the gauge length compensates for specimen heat losses occurring to the grips as they hold the specimen. While a properly designed furnace system produces a uniform temperature throughout the gauge length, the available heating rate produced by the furnace is substantially slower than those needed for simulating many manufacturing and fabrication processes.

Induction heating, which imparts more localized specimen heating than attainable through a furnace, yields heating rates which are considerably faster than those typically provided by a furnace. Here, an induction coil is placed around and covers the specimen gauge length and heats the specimen material through high frequency induction. The coils of an induction heater are shaped to provide additional heating capability to the ends of the gauge length to compensate for heat losses to the grips. While this scheme tends to adequately function, acceptable results generally occur only after significant effort has been expended on a trial-and-error basis to properly position the induction coils relative to the gauge length. Thus, an operator often needs to have considerable skill in that regard to properly utilize induction heating. Further, the induction coils tend to create localized hot spots within the specimen gauge length. Consequently, a resulting temperature distribution along the gauge length will not be as uniform as would occur with a furnace.

Fastest yet is direct self-resistance heating mechanisms where heating current is passed directly through the specimen and the specimen self-resistively heats. While self-resistance heating is the most versatile, by virtue of its very high heating rates, and adaptable of the three heating techniques, it is typically the most difficult to control. Given its relatively fast heating rate, self-resistance heating can be used to reproduce thermal characteristics, in a metallic test specimen, which are inherent in a wide variety of metal manufacturing processes and applications.

Typically, in existing thermo-mechanical test systems, both electrical and mechanical connections are made to the same locations on the specimen, i.e., where the specimen is held at its opposing ends by a pair of grips. Consequently, self-resistive heating currents flow between the grips and end-to-end through the specimen. Each grip is typically water cooled or mounted in a water cooled jaw system to prevent that grip from overheating and being damaged during a test. Inasmuch as the current flow is substantially uniform across any specimen cross-section taken transverse to the axial current flow through the specimen, then essentially isothermal crosswise planes are established through the specimen. However, owing to its reduced cross-sectional area, the gauge length will have a higher electrical resistance than the specimen end sections. When the electrical current flow is high, as required to keep the specimen at relatively high temperature between a relatively cool jaw system, thermal currents flow primarily from a reduced diameter gauge length to larger-diameter specimen end sections. Consequently, in traditional direct resistance heating methods and as a result of applying the heating current, the specimen typically has its highest temperature at its midpoint and its coldest temperature at its ends where the mechanical grips are located, hence causing a thermal gradient to appear from the mid-point to each end of the specimen. While a steep thermal gradient is useful for some types of tests such as weld heat-affected zone simulations, it is not desirable in certain other types of tests such as thermal mechanical fatigue tests. To compensate for heat losses on the ends of the specimen and hence reduce the gradients, grips have been developed which exhibit reduced contact area with the specimen and thus produce reduced specimen cooling. While this approach creates a more uniform temperature distribution along the specimen length, it adversely affects various mechanical properties of both the grips and the specimen, particularly where the grips attach to the specimen which, in turn, prevents these grips from being used effectively for many types of tests. Furthermore and of significant consequence, since the current and mechanical attachment points are the same, grip designs which reduce the thermal gradients create a more uniform temperature over the entire length of the specimen and not just over the gauge length. By heating the specimen section between the gauge length and each grip to a similar temperature as the gauge length, that section is weakened which, in turn, allows unwanted deformation to occur in that section during a concurrent mechanical test program, thereby possibly distorting the results of that test program.

Currently, the GLEEBLE material testing systems manufactured by Dynamic Systems Inc. of Poestenkill, N.Y. (which also owns the registered trademark "GLEEBLE") are dynamic thermo-mechanical material testing systems that utilize a computer-controlled servo-hydraulic mechanical system to controllably strain and/or deform a specimen along with a self-resistive heating system to controllably produce essentially cross-wise isothermal planes through the specimen, thus permitting both mechanical and thermal programs to be imparted to the specimen. In these systems, self-resistive heating is accomplished by using two electrically and thermally conductive jaw/anvil assemblies or other appropriate grip systems, each of which securely holds an opposing end of the specimen, with a reduced diameter work zone there between. Large flexible conductors provide a path for large electrical heating currents between the jaw/anvil assemblies and an electrical power supply. Each jaw/anvil assembly is electrically isolated from the remainder of the mechanical system to prevent electrical heating currents from flowing through the latter and bypassing the specimen. However, inasmuch as the heating current used in even these systems flows end-to-end through the specimen, specimen end sections adjacent to the gauge length may experience unwanted deformation during certain thermo-mechanical test programs.

Moreover, a majority of material testing systems currently in use, other than the GLEEBLE systems, and which have a servo-controlled hydraulic mechanical system, possess no inherent specimen heating capability. Such testing systems simply perform mechanical test programs on specimens which remain at room temperature. While appropriate and commercially available induction heating systems and furnaces can be added to these testing systems to provide some degree of specimen heating, neither of these modalities is as responsive or controllable, and hence as useful as a self-resistance heating system.

Accordingly, a need exists in the art for a technique, including apparatus and accompanying methods, which can be readily adapted to a conventional mechanical testing system in order to impart a much-needed thermal capability to self-resistively heat a metallic specimen under test and particularly to apply heating current along the gauge length but without appreciably heating the grips of specimen sections outside the gauge length and thus substantially prevent unwanted deformation. Preferably, the apparatus should not appreciably, if at all, alter any of the mechanical capabilities of a conventional testing system and should also be suitable for use in conventional thermo-mechanical test systems that already employ direct resistance specimen heating.

SUMMARY OF THE INVENTION

In accordance with the teachings of the present invention, this need is advantageously met by attaching a pair of, e.g., conductive collars to the specimen in a fashion that bridges (straddles) the gauge length but with the collars being located inward of the grips in order to pass heating current through the gauge length but not through each specimen end section situated between an end of the gauge length and each grip. The collar is typically a ring of conductive material sized to tightly fit around and abut against and electrically contact a portion of the outer cylindrical surface of the specimen, and secured to the specimen, i.e., a contact area, by, e.g., mechanical fasteners, such as screws or bolts, or a spring-loaded device, in order to fully contact a specimen surface and thereby uniformly pass heating current from the power source to the specimen.

By appropriately selecting the material for the conductive collar to have an appropriate resistivity and dimensioning the collar appropriately, including properly sizing the contact area between each collar and the specimen surface, then, for a given amount of heating current, passing through the collars, the contact areas and the gauge length, the collars, including their contact areas, will self-resistively heat and impart additional heat to the gauge length in order to yield a desired thermal gradient in the gauge length, but without appreciably heating either the end sections of the specimen lying outside the collars or the grips. The desired gradient can either be relatively small or essentially zero. Each collar is typically formed of a material that has a much higher resistivity than that of the specimen.

For a given amount of heating current and as with any conductor, the self-resistive heating generated by the specimen and each of the collars is proportional to the resistance of each; the higher the resistance, the more heat that is generated. Because each collar encircles and abuts against the specimen adjacent to each end of the specimen gauge length but on a shoulder portion of the specimen that has a larger diameter and hence a lower resistance than the gauge length, additional heating is required along an interface region, i.e., the contact area, between the collar and the specimen surface to prevent heat loss at the collar that would otherwise yield an undesirable thermal gradient in the specimen gauge length. With the collar made of a material having a sufficiently high resistance relative to that of the specimen, then the collar as well as along the entire contact area, due to contact resistance all along that area, will collectively generate a sufficient amount of additional self-resistive heat to substantially eliminate this gradient or reduce it to a relatively low desired amount. When the temperature along the contact area exceeds that of the specimen itself—owing to the additional heat, then heat flows from the heated collar, through the gauge length, and into the specimen. Hence, heat flow outward from the contact area into the specimen will cancel heat flow coming back from the heated gauge length. Moreover, this additional heat will also compensate for any surface heat loss occurring in the ends and surface of the specimen and heat losses occurring through the insulation at the mechanical jaws, thus further eliminating or at least reducing any thermal gradients. Consequently, a rather uniform temperature distribution occurs across the entire gauge length as the specimen heats and a much lower temperature in the specimen end section located between each collar and a grip—when compared to temperatures that occur in specimen portions located outside the gauge length but resulting from use of conventional direct resistance heating methods.

If a particular lengthwise thermal gradient is desired in the specimen as it heats, then, for a corresponding amount of heating current, the resistance and/or dimensions of the collar material and/or of the contact areas can be chosen accordingly to impart an appropriate level of additional heat to the specimen to generate that gradient.

Inasmuch as the grip attached to each end of the specimen is electrically insulated from the specimen along its attachment (gripping) area, no heating current passes in each specimen end section, i.e., in a region between that portion of the specimen lying between a collar and its proximate grip, hence producing no self-resistive heating in that portion. Consequently, that portion of the specimen has a much lower temperature than the gauge length thereby maintaining the strength of the specimen near its ends and causing any mechanical deformation, that would subsequently occur during a concurrent mechanical test program, to concentrate along the gauge length. This, advantageously and substantially prevents unwanted deformation from occurring during mechanical and thermal test programs in either of the specimen end sections.

Through the present invention, the mechanical and thermal systems in the overall testing system are separated from each other and can independently function of each other in order to provide enhanced control of each. As such and advantageously, the mechanical system can be designed to provide very stiff mechanical support and the thermal system can be designed to generate very small thermal gradients, if any at all, along the gauge length, thus substantially preventing unwanted mechanical deformation in the specimen end sections.

As a feature of the invention, the inventive technique can be readily applied to use with torsion specimens by simply modifying the specimen grips to impart relative rotation between the ends of the specimen rather than just applying tensile and/or compressive forces along a longitudinal axis of the specimen. The collars and their electrical connections need not be changed.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where appropriate, to designate identical elements that are common to the figures.

DETAILED DESCRIPTION

After considering the following detailed description, those skilled in the art will clearly realize that the broad teachings of the invention can be readily and advantageously utilized in conjunction with any one of a wide variety of material testing systems used for thermo-mechanical testing and physical simulation to impart a self-resistive specimen heating capability to those systems. Such testing systems would include not only tension and compression systems but also torsion systems. The self-resistive heating capability is well suited to replace induction and furnace heating systems commonly used to obtain essentially zero thermal gradients along a specimen gauge length. Moreover, even apart from its use with testing systems, the present invention can be used across a wide variety of industrial heating applications to produce localized self-resistive heating in conductive materials, such as, for example, to provide heat treatment to a metallic object either in a production or laboratory environment.

For purposes of illustration and to simplify the ensuing discussion, the invention will be described in the context of use with illustratively the jaw system of a GLEEBLE dynamic thermo-mechanical material testing system of the type currently manufactured by Dynamic Systems, Inc. of Poestenkill, N.Y. (which also owns the registered trademark "GLEEBLE").

Figure 1:
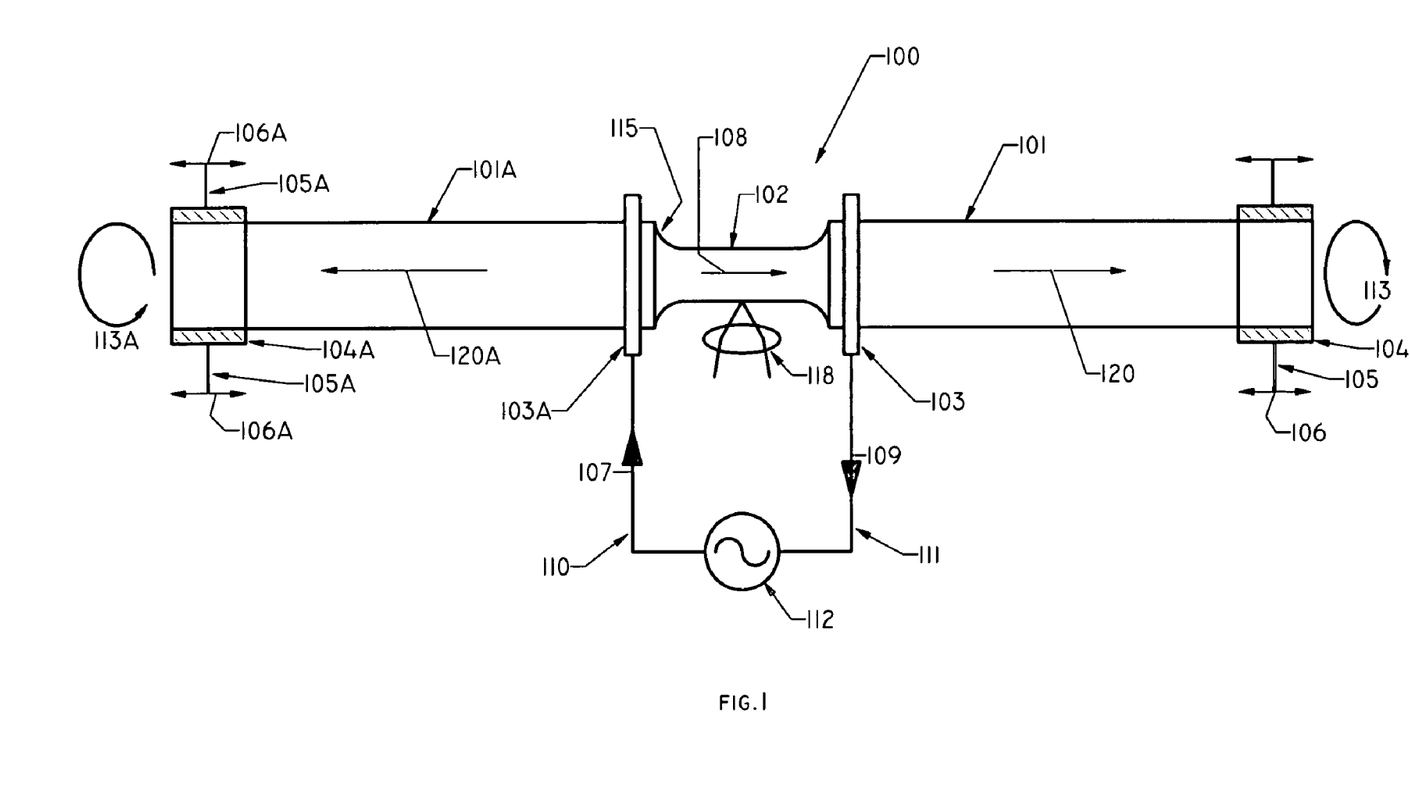
FIG. 1 depicts a simplified schematic diagram of thermal and electrical current flow during self-resistive heating of a specimen gauge length that occurs through use of the present inventive teachings.

FIG. 1 depicts a simplified schematic diagram of thermal and electrical current flow during self-resistive heating of a gauge length of a metallic specimen, the heating being conducted in accordance with the teachings of the present invention.

As shown, specimen 100, in the form of a cylindrical rod, has enlarged ends 101 and 101A (also referred to herein as "specimen end sections") and, at its mid-span, a reduced diameter work zone (also called "gauge length") 102. Illustratively, this specimen, particularly for thermal-mechanical fatigue testing, is often configured as a cylindrical bar approximately 120 mm long, with a 10 mm diameter and a work zone of approximately 15 mm in length and 8 mm in diameter. This specimen configuration is typical of many specimens used in materials testing and physical simulation with the GLEEBLE systems as well as with many other conventional materials testing systems.

Electrical current is applied to opposing portions of the specimen through conductive collars 103 and 103A, each of which abuttingly engages along a circumferential portion of an external surface of the specimen proximate to a shoulder situated at a corresponding one of two opposing ends of gauge length 102.

For one half of an applied AC power cycle, the electrical current path is, as shown by arrows 107, 108 and 109, from current source 112 through conductor 110 to collar 103A through gauge length 102 to collar 103, and from there through conductor 111 and back to source 112. Current flow will simply reverse its direction during the other half of the applied AC power cycle. While the voltage produced by source 112 is rather low, typically in the range of 3-20 volts, the heating current is quite large, typically in the range of hundreds to thousands of amperes. Since collars 103 and 103A are situated on the large diameter of specimen 100, electrical current flows through the large diameter at each end of gauge length 102 and its adjacent shoulder region (one of which 115 is specifically referenced). Inasmuch as the ends of the specimen are electrically insulated by insulators 104 and 104A from the remainder of the test system (not shown for simplicity), then no electrical current will flow through end sections 101 and 101A of the specimen.

The electrical current causes the gauge length to self-resistively heat in proportion to the square of the current multiplied by the electrical resistance of the gauge length. Thermocouple 118, attached to the center of a specimen mid-span, measures the temperature of the test region with its output being routed to an external conventional temperature control system (not shown) used in regulating the current applied to the specimen.

Since no electrical current flows in the ends of the specimen, the only heat present in the ends of the specimen is due to thermal conduction, as represented by arrows 120 and 120A, from the heated area near collars 103 and 103A towards the ends of the specimen.

Generally speaking and for any conductor, the amount of heat produced in that conductor from self-resistive heating (also called "bulk heating") equals the square of the electrical current flowing through that conductor multiplied by the resistance per unit length of the conductor. If the cross-sectional area of the conductor varies—as is the case here with reduced diameter with gauge length 102 as compared to specimen end sections 101 and 101A, then the resistance will decrease as that area increases. Consequently, for a constant current flow, any increase in area in a given portion of the conductor will decrease the resistance and hence proportionally reduce the resulting self-resistive heating produced in that portion.

As the resistivity of the conductor increases or decreases—through use of a different material for the conductor, so too will its resistance per unit length, and hence, for a constant current applied through that conductor, the self-resistive heat generated thereby will proportionally increase or decrease, respectively.

Thus, to yield a desired amount of self-resistive heating for a given current flow through a conductor, the conductor can be formed from a material having an appropriate resistivity and/or by modifying its cross-sectional area.

Advantageously and in accordance with the broad inventive teachings, through heat generated by collars 103 and 103A as well as by the contact areas (due to contact resistance) between each collar and the specimen surface, axial thermal gradients that would normally arise in the gauge length of the specimen, whenever that specimen were to be subjected to self-resistive heating, can be set to a desired amount or even substantially, if not totally, eliminated.

The gauge length, due to its decreased cross-sectional area as compared to the remainder of the specimen, has a higher resistance than adjacent portions of the specimen. Consequently, for a given amount of heating current, the gauge length will reach a desired test temperature before those portions will. Thus, the temperature of the gauge length will dictate and thus limit the amount of the heating current to use and a total duration during which that current is applied to the specimen. Once the gauge length has reached the desired temperature, no further heating is needed and hence no further heating current needs to be applied to the specimen (other than to compensate for any heat losses and thus hold the gauge length at temperature during a mechanical test program). Inasmuch as the required heat produced by both collars is generated only through application of this current, the collar material must be chosen to have an appropriate amount of resistance in order to generate the proper amount of heat from just that current.

The amount of electrical self-resistive heating current is limited by the desired heating effect that is to occur in the gauge length and the maximum temperature desired for a given thermal test program. The electrical resistivity of the specimen is dependent upon specimen geometry and specimen material. The collar material and size, including the size of its contact area with the specimen surface, can be selected to impart a desired amount of additional self-resistive heat to the specimen for the limited self-resistive heating current flowing through the collars, the contact areas and the gauge length. In that regard, due to contact resistance, the contact areas themselves will generate self-resistive heat due to the passage of the heating current there through. Depending on its magnitude, this heat can effectively reduce any axial thermal gradients caused by self-resistive heating of the gauge length to a desired level or substantially, if not totally, eliminate any such gradients. Consequently, the thermal gradients axially occurring along the gauge length of the specimen can be controlled based on the additional self-resistive heat generated by the current flow through the collars and the contact areas.

In particular, collars 103 and 103A are typically formed from a material, such as graphite, that has a relatively high electrical resistivity compared to that of the specimen. As a consequence, the amount of self-resistive heat generated in both collars is rather large. The increased heat present at the contact area between each collar and the specimen surface permits heat to flow from each collar, through that area to the specimen surface proximate to each end of gauge length 102. This heat is added to the self-resistive heating produced by the electrical current flowing through the gauge length itself. The self-resistive heat generated from the collars, including that generated through the contact resistance alone, compensates for axial heat flow (loss) that would otherwise arise from heated gauge length 102. Further, heat that is lost axially to specimen end sections 101 and 101A, as indicated by arrows 120 and 120A, is primarily supplied by the collars, not the heated gauge length, thus permitting the gauge length to remain at a substantially uniform temperature throughout. This heat loss is due to surface losses and loss through insulators 104 and 104A. The heat loss in the ends results in the ends of the specimen being cooler than gauge length 102. The heat produced by both collars can be set, in light of the anticipated maximum current flow through the specimen, by forming the collars from a material having an appropriate resistivity and with an appropriate cross-sectional area and with a suitably sized contact area. Since the contact resistance is often much lower than the resistance of each collar, the additional heat generated by the former will be less than that due to the latter.

Lines 105 and 105A represent mechanical connections from insulators 104 and 104A to the remainder of the testing system. As indicated by arrows 106 and 106A, this system typically applies tensile or compressive mechanical motion, through the insulators, to the ends of the specimen in order to controllably deform the gauge length. As shown by circular arrows 113 and 113A, this mechanical motion may be torsional (differential end-to-end rotation) or have torsional components.

Figure 2:
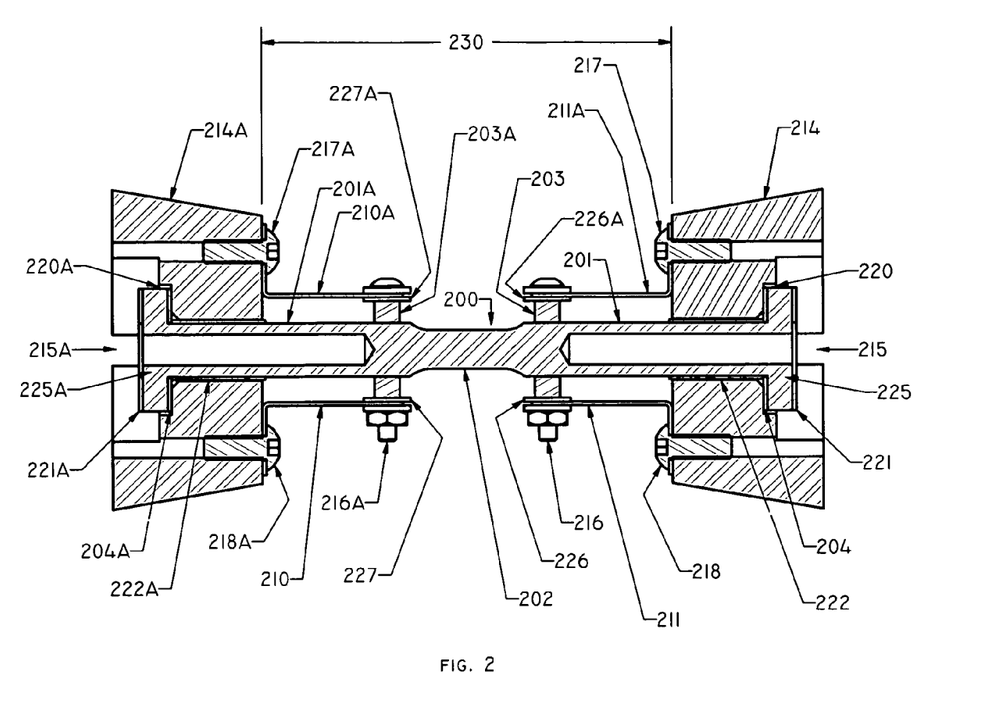
FIG. 2 depicts a detailed section view of one embodiment of the inventive apparatus taken along lines 2-2 shown in FIG. 4.
Figure 3:
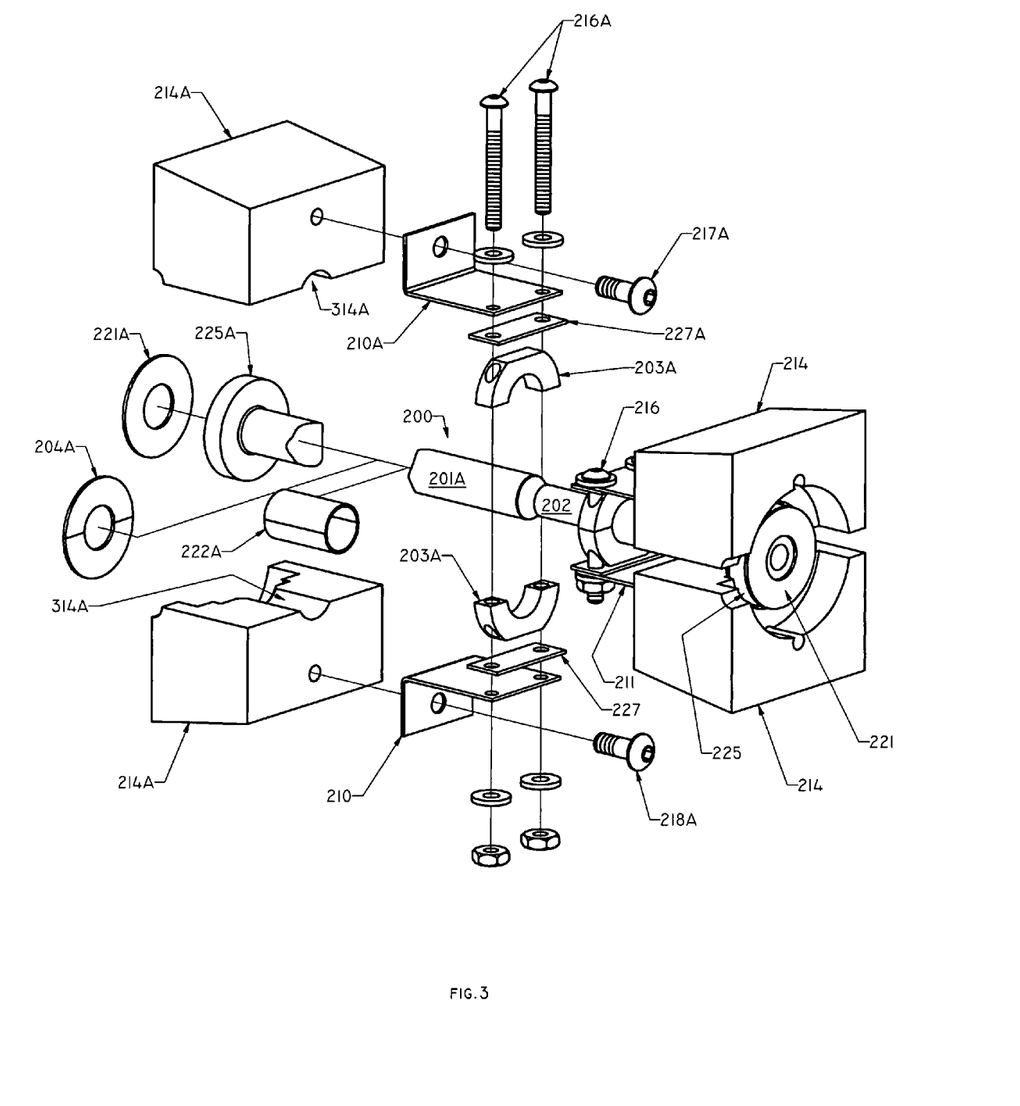
FIG. 3 depicts a partially exploded view of the various parts of the apparatus shown in FIG. 2.
Figure 4:
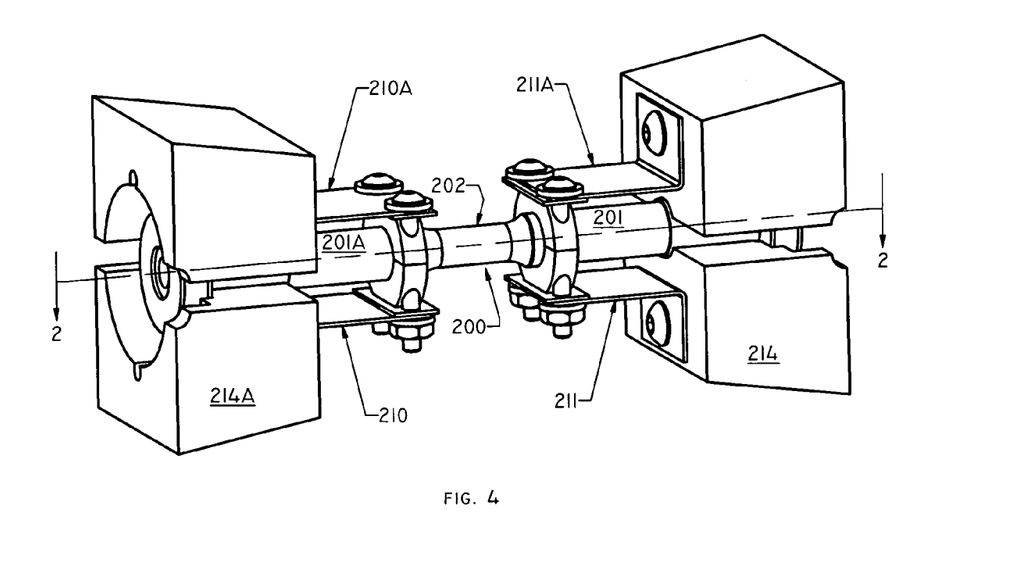
FIG. 4 depicts a perspective view of the inventive apparatus, once assembled, shown in FIGS. 2 and 3.

FIGS. 2-4 each shows a different view of one embodiment of the present invention. Specifically, FIG. 2 provides a detailed sectional view taken along the longitudinal axis of the specimen and as indicated by lines 2-2 shown in FIG. 4. FIG. 3 provides a partially exploded view in which collar 203A, metallic conductors 210 and 210A and fasteners 216A have been separated for clarity; and FIG. 4 depicts a perspective view. As these figures will now be collectively discussed, the reader should simultaneously refer to all three figures throughout the following discussion.

Specimen grips 214 and 214A are of the type conventionally used in the GLEEBLE system and as illustratively described in U.S. Pat. No. 5,202,542 (issued to H. Ferguson on Apr. 23, 1993) (hereinafter the '542 patent). For the embodiment shown in FIG. 2, wedge jaws 214 and 214A are placed in suitably tapered cavities located in a main jaw assembly (not shown in the figure, but described in the '542 patent). Suitable hydraulic jacks (well known and not shown) press against electrical insulators 221 and 221A situated on opposing ends of specimen 200 to securely hold the specimen in place during tension and compression, thus defining specimen region 230 lying between the grips. To apply further compressive force to the specimen to deform the gauge length, additional force is applied to insulators 221 and 221A by servo-controlled hydraulic actuators (also well known and not shown). As a result, jaws 214 and 214A are forced toward each other and, by doing so, squeeze their respective specimen ends together.

Insulators 204 and 204A, 221 and 221A, and 222 and 222A together with air gaps 220 and 220A situated between the specimen ends and jaws 214 and 214A, respectively, electrically insulate both jaws from the specimen (i.e., along its attachment (gripping) areas) so that no electrical current flows between the jaws and the specimen ends. Collectively, these insulators and the air gaps also limit thermal loss from those ends into the jaws. Each of air gaps 220 and 220A may be replaced by a suitable insulator.

As shown in detail in FIG. 3, insulator 204A is a split washer which is placed over end section 201A and slid into place against specimen endpiece 225A. Insulator 221A is an insulating washer which is placed on a corresponding end of the specimen. Insulator 222a is an insulating collar, also being split and sufficiently long, slid over the end section 201A and slid into place against insulator 204A in order to prevent that section from establishing electrical contact with a surface of inner bore 314A of jaw 214A. Insulators 204 and 221 are identical to insulators 204A and 221A, respectively; collar 222 is identical to collar 222A. Jaws 214 and 214A are preferably formed from a metal, such as stainless steel or titanium, that has a higher electrical and thermal resistance than the specimen, thus further limiting thermal losses from the specimen.

Collars 203 and 203A, which route self-resistive heating current to the specimen, are fabricated from, e.g., graphite (though other materials having appropriate electrical resistivity and heat tolerance can be used instead). Each of these collars takes the form of a thick washer split across its diameter, into separate half-collars, to readily permit its mounting on the specimen. Conductive sheet strips 210 and 210A, 211 and 211A are in abuttingly electrical contact with and route heating current between both jaws and the collars 203A and 203, respectively. Each of the collars may be appropriately shaped, such as with flat surfaces (as shown in FIG. 3), to facilitate its abutting connection. As shown, each half-collar has rounded ends on its outer surface. Each of conductive reinforcing strips 226, 226A, 227 and 227A is placed between each half-collar in collars 203 and 203A, and its respective conductive sheet strip 211, 211A, 210 and 210A. As a result, screws 216 and 216A compress conductive sheet strips 210 and 210A which, in turn, compress, through the reinforcing strips, each half-collar, at its centerline, onto the specimen. This arrangement provides sufficient spring force between the conductive sheet strips and the half-collars to accommodate heat and thermal expansion, thus maintaining proper pressure against the specimen at elevated temperatures so as to assure adequate abutting electrical and thermal contact occurs between each half-collar and the specimen. Each of the conductive sheet strips may be formed of, e.g., austenitic stainless steel, a molybdenum-based alloy or a nickel-based alloy. For austenitic stainless steel, the sheet strips are typically 1 mm (0.040 inches) thick by approximately 2.5 cm (1 inch) wide. Conductive strips 210 and 210A, and 211 and 211A are secured to reinforcing strips 227 and 227A, and 226 and 226A, and collars 203A and 203 using bolts 216 and 216A (with appropriate nuts and washers), respectively, to ensure a secure electrical and mechanical connection between the sheet strips, the reinforcing strips, the collars and the specimen end sections. The conductive strips are attached to jaws 214 and 214A by pairs of threaded fasteners 217 and 218 and 217A and 218A, respectively, or alternately through springs or other suitable attachment methods. Each of the reinforcing strips may be formed of, e.g., a molybdenum-based alloy or a nickel-based alloy, as both retain high strength at elevated temperatures. The reinforcing strips may be omitted from the assembly if the conductive sheet strips are themselves sufficiently strong at the test temperatures to retain their shape and still provide proper force on the collars. In this instance, the collars may also have rectilinear rather than rounded outer surfaces. Furthermore, each reinforcing strip creates another resistive interface which can be used, through its contact resistance at this interface, to generate additional local heating. Moreover, the reinforcing strip itself provides even further additional self-resistive heating based on its own resistance. All this additional heat can offset heat losses to the sheet strip due to heat generated by and flowing from the collar itself.

Each pair of conductive strips 210 and 210A, and 211 and 211A could be replaced by a suitable clamp positioned around collar 203 and 203A, respectively, and a flexible electrical cable connected, at one of its ends, to the collar, with the cable also being connected, at its other end, to an appropriate terminal of power supply that provides the self-resistive heating current.

With the inventive apparatus shown in FIGS. 2-4, the electrical current path through the apparatus, starting from jaw 214, is then through conductive strips 211 and 211A through collar 203, through specimen gauge length 202, through collar 203A, through conductive strips 210 and 210A, and finally into jaw 214A. Jaws 214 and 214A are connected, through a main jaw system (not shown) of the GLEEBLE system, to a suitable conventional power source (also not specifically shown), which supplies the heating current. No electrical current flows in end sections 201 and 201A, extending outward beyond the collars, due to insulators 204 204A, 218, 218A, 221 and 221A, and air gaps 220 and 220A.

Holes 215 and 215A, which may be optionally bored in the ends of the specimen, are typically used to increase a cooling rate of the specimen during appropriate parts of a thermal program. An increased cooling rate may be accomplished by forcing air or water into the far ends of these holes.

In the exploded view provided in FIG. 3, collar 203A, metallic conductors 210 and 210A and fasteners 216A have been separated for added clarity and understanding. Similarly, jaw 214 has been separated to show insulators 204A, 221A and 222A.

Illustratively, I have fabricated collars 203 and 203A from fine grade graphite material (commercially known as "Rescor 56L") with a 10 mm inside diameter and a thickness of 5 mm. Each of these collars has an outside diameter of 23 mm. When used with a typical stainless steel specimen with a gauge length of 8 mm diameter and a length of 15 mm long as described above, the inventive heating method yielded a uniform temperature within the gauge length that, at 1000° C., had less than a 5° C. variation (which, for all practical purposes and relative to the gauge length temperature, represents a substantially zero thermal gradient) over the entire gauge length. Of course, other specimen sizes can be used and the collar size can be adjusted to produce the same or similar results.

While the invention has been shown and described using the jaws of the GLEEBLE system, other types of jaws, chucks, clamps or mechanical connecting devices may be used to adequately mount the specimen along with the inventive apparatus into other types of mechanical tension, compression and/or torsion material testing machines. Further, while conductive collars 203 and 203A have been shown and described, these collars themselves can be replaced by other types of appropriate conductive elements, such as conductive clamps, that will provide a strong abutting electrical contact between the conductive strips and the specimen. However, since a collar provides a smoother interface between it and the specimen than will a clamp, use of a collar is likely to yield a more uniform generation of heat along the interface than will a clamp, thus further reducing the formation of any thermal gradients. Obviously, the geometry of whatever conductive elements are used will be dictated, in good measure, by the cross-sectional geometry of the specimen itself.

Although a single preferred embodiment which incorporates the teachings of this present invention has been shown and described in detail herein, those skilled in the art can readily devise many other varied embodiments that still incorporate these teachings.

The invention claimed is:

1. Apparatus for direct resistance heating of a metallic object, the apparatus comprising:
   first and second mechanical devices for securely holding the object along corresponding first and second attachment areas thereon; and
   first and second conductive devices for making abutting electrical contact with the object along first and second contact areas, respectively, on a surface of the object and routing electrical self-resistive heating current through a gauge length of the object situated between the first and second contact areas so as to self-resistively heat the gauge length, the first and second conductive devices being situated on the object inward of the first and second attachment areas, respectively, and spanning the gauge length and within a region of the object bridged by the first and second attachment areas thereby defining first and second end sections of the object situated between the first and second attachment areas and the first and second contact areas, respectively; and
   wherein said first and second mechanical devices are suitably configured such that the heating current flows between the first and second contact areas and through the gauge length and each of the first and second conductive devices has an appropriate pre-defined resistance and is suitably dimensioned such that for a specified amount of the heating current passing through the first and second conductive devices, the first and second contact areas and the gauge length, the first and second conductive devices self-resistively heat and impart additional heat to the object beyond that generated in the gauge length in order to produce a pre-defined thermal gradient across the gauge length but without self-resistively heating the first and second end sections of the object.

2. The apparatus in claim 1 wherein the object is a metallic specimen, and the first and second mechanical devices hold the specimen at opposing ends thereof and impart controlled amounts of compressive, tensile or torsional force to the specimen in order to deform the gauge length.

3. The apparatus in claim 2 wherein the first and second mechanical devices comprises jaws, chucks or clamps for use in a thermo-mechanical testing system.

4. The apparatus in claim 3 wherein each of the first and second conductive devices comprises a conductive collar or conductive clamp.

5. The apparatus in claim 4 wherein the resistance of each of the first and second conductive devices is higher than a resistance of the object.

6. The apparatus in claim 5 wherein the first and second mechanical devices are electrically conductive and are attached to the first and second conductive devices by first and second conductive elements, respectively, and where the first and second mechanical devices are electrically insulated from the object and along the first and second attachment areas such that the heating current is routed to the object via the first and second conductive elements and the first and second conductive devices but not through the first and second end sections.

7. The apparatus in claim 6 wherein each of the first and second conductive devices is manufactured from graphite.

8. The apparatus in claim 7 wherein the predefined thermal gradient is substantially zero.

9. The apparatus in claim 8 wherein each of the first and second conductive elements comprises at least one conductive strip.

10. The apparatus in claim 8 wherein each of the first and second conductive devices further comprises a cable connected, at one end, thereto to the first or second conductive device and with a second end of the cable being connected to a suitable power supply that provides the heating current.

11. The apparatus in claim 1 wherein each of the first and second conductive devices comprises a conductive collar or conductive clamp.

12. The apparatus in claim 11 wherein the resistance of each of the first and second conductive devices is higher than a resistance of the object.

13. The apparatus in claim 12 wherein the first and second mechanical devices are electrically conductive and are attached to the first and second conductive devices by first and second conductive elements, respectively, and where the first and second mechanical devices are electrically insulated from the object and along the first and second attachment areas such that the heating current is routed to the object via the first and second conductive elements and the first and second conductive devices but not through the first and second end sections.

14. The apparatus in claim 13 wherein each of the first and second conductive devices is manufactured from graphite.

15. The apparatus in claim 14 wherein the pre-defined thermal gradient is substantially zero.

16. The apparatus in claim 1 wherein the resistance of each of the first and second conductive devices is higher than a resistance of the object.

17. The apparatus in claim 16 wherein the first and second mechanical devices are electrically conductive and are attached to the first and second conductive devices by first and second conductive elements, respectively, and where the first and second mechanical devices are electrically insulated from the object and along the first and second attachment areas such that the heating current is routed to the object via the first and second conductive elements and the first and second conductive devices but not through the first and second end sections.

18. The apparatus in claim 17 wherein each of the first and second conductive devices is manufactured from graphite.

19. The apparatus in claim 18 wherein the pre-defined thermal gradient is substantially zero.

20. The apparatus in claim 19 wherein each of the first and second conductive devices further comprises a cable connected, at one end, thereto to the first or second conductive device and with a second end of the cable being connected to a suitable power supply that provides the heating current.

21. A method for use in direct resistance heating of a metallic object comprising the steps of:

securely holding the object, via first and second mechanical devices, along corresponding first and second attachment areas thereon; and making abutting electrical contact, through first and second conductive devices, with the object along first and second contact areas, respectively, on a surface of the object and routing electrical self-resistive heating current through a gauge length of the object situated between the first and second contact areas so as to self-resistively heat the gauge length, the first and second conductive devices being situated on the object inward of the first and second attachment areas, respectively, and spanning the gauge length and within a region of the object bridged by the first and second attachment areas thereby defining first and second end sections of the object situated between the first and second attachment areas and the first and second contact areas, respectively; and passing a specified amount of heating current through the first and second conductive devices so as to self-resistively heat the gauge length; and wherein said first and second mechanical devices are suitably configured such that the heating current flows between the first and second contact areas and through the gauge length and each of the first and second conductive devices has an appropriate pre-defined resistance and is suitably dimensioned such that for the heating current passing through the first and second conductive devices, the first and second contact areas and the gauge length, the first and second conductive devices self-resistively heat and impart additional heat to the object beyond that generated in the gauge length in order to produce a pre-defined thermal gradient across the gauge length but without self-resistively heating the first and second end sections of the object.

22. The method in claim 21 wherein the object is a metallic specimen, and the method further comprises the steps of:

holding the specimen, via the first and second mechanical devices, at opposing ends thereof; and imparting, through the first and second mechanical devices, controlled amounts of amounts of compressive, tensile or torsional force to the specimen in order to deform the gauge length.

23. The method in claim 22 wherein the pre-defined thermal gradient is substantially zero.

* * * * *